US011631316B2

United States Patent
Yu et al.

(10) Patent No.: US 11,631,316 B2
(45) Date of Patent: Apr. 18, 2023

(54) IN-VEHICLE LIFE DETECTION SYSTEM AND DETECTION METHOD THEREOF

(71) Applicant: CUB ELECPARTS INC., Changhua County (TW)

(72) Inventors: San-Chuan Yu, Changhua County (TW); Yu-Tao Yu, Changhua County (TW); Yuan-Tung Hung, Changhua County (TW); Ming-Hung Lin, Changhua County (TW); Wei-Shun Shih, Changhua County (TW)

(73) Assignee: CUB ELECPARTS INC., Changhua County (TW)

( * ) Notice: Subject to any disclaimer, the term of this patent is extended or adjusted under 35 U.S.C. 154(b) by 292 days.

(21) Appl. No.: 16/869,398

(22) Filed: May 7, 2020

(65) Prior Publication Data

US 2020/0372782 A1    Nov. 26, 2020

(30) Foreign Application Priority Data

May 20, 2019 (TW) .................................. 108117268

(51) Int. Cl.
*G08B 21/24*    (2006.01)
*B60R 25/01*    (2013.01)
(Continued)

(52) U.S. Cl.
CPC .............. *G08B 21/24* (2013.01); *B60R 25/01* (2013.01); *B60W 40/08* (2013.01); *E05B 81/64* (2013.01); *B60W 2420/52* (2013.01); *B60W 2510/06* (2013.01); *B60W 2510/30* (2013.01); *B60W 2540/01* (2020.02)

(58) Field of Classification Search
CPC ......... A61B 5/11; A61B 5/113; A61B 5/6893; A61B 5/746; B60R 25/01; B60W 2420/52; B60W 2510/06; B60W 2510/30; B60W 2540/01; B60W 40/08; E05B 81/64; G01S 13/04; G08B 21/24; G08B 25/08; G08B 3/10; G08B 5/36
See application file for complete search history.

(56) References Cited

U.S. PATENT DOCUMENTS 6,937,143 B2 *  8/2005  Ohtaka .............. B60R 21/01546
                                              73/1.01
7,626,492 B2 * 12/2009  Sugiura ..................... G01J 5/34
                                              600/300
(Continued)

*Primary Examiner* — Babar Sarwar
(74) *Attorney, Agent, or Firm* — Muncy, Geissler, Olds & Lowe, P.C.

(57) ABSTRACT

An in-vehicle life detection system and detection method thereof are provided. The system includes a processor, an electromagnetic wave detection module, and a warning module. The method includes following steps: vehicle condition identifying step, life form detecting step, and warning step. Upon receiving an engine off signal and a driver absence signal, the processor emits a detection activation signal, activating the electromagnetic wave detection module to emit an electromagnetic wave for detecting a life form. When the life form is detected, the warning module sends a warning signal, indicating that the life form is left in the vehicle when the vehicle is in the engine off status with the doors closed. Thus, the tragedy of a life form remaining inside the vehicle incapable of calling for help is avoided.

11 Claims, 7 Drawing Sheets

(51) Int. Cl.
  *B60W 40/08*  (2012.01)
  *E05B 81/64*  (2014.01)

(56) References Cited

U.S. PATENT DOCUMENTS

| | | | | |
|---|---|---|---|---|
| 9,266,535 | B2* | 2/2016 | Schoenberg | G08B 25/005 |
| 9,845,050 | B1* | 12/2017 | Garza | G08B 21/0205 |
| 11,097,659 | B1* | 8/2021 | Abdelhamid | B60N 2/002 |
| 11,151,861 | B2* | 10/2021 | SungTae | G08B 21/0247 |
| 11,198,388 | B1* | 12/2021 | Crose | B60N 2/002 |
| 11,250,685 | B2* | 2/2022 | Taylor | G01S 13/931 |
| 2002/0171540 | A1* | 11/2002 | Ando | B60N 2/002 340/425.5 |
| 2017/0267169 | A1* | 9/2017 | Fleurence | B60Q 3/74 |
| 2018/0319291 | A1* | 11/2018 | Dicanosa | B60Q 9/00 |
| 2019/0019392 | A1* | 1/2019 | Lu | G08B 21/24 |
| 2019/0143944 | A1* | 5/2019 | Park | G01S 13/878 340/426.24 |
| 2020/0290567 | A1* | 9/2020 | Funyak | B60R 25/34 |
| 2020/0309932 | A1* | 10/2020 | Zeng | H01Q 1/3241 |
| 2021/0008959 | A1* | 1/2021 | Lee | B60H 1/00978 |
| 2021/0186336 | A1* | 6/2021 | Bellifemine | A61B 5/01 |
| 2021/0280042 | A1* | 9/2021 | SungTae | G08B 21/0225 |

* cited by examiner

IN-VEHICLE LIFE DETECTION SYSTEM AND DETECTION METHOD THEREOF

BACKGROUND OF THE INVENTION

1. Field of the Invention

The present invention relates to in-vehicle life safety mechanisms, and more particularly, to an in-vehicle life-detection system and method thereof.

2. Description of the Related Art

A conventional safety system for prevention of in-vehicle accidental locking of life form includes a detection unit, a warning unit, and a limitation member. When an operation of a passenger protection device is detected, the warning unit locks the vehicle key in the key hole, such that the driver is unable to pull out the key and thus reminded of that passenger is still in the vehicle. However, even if the driver is unable to pull out the key, the driver is still able to open the door and leave the vehicle, so that the passenger is still possible to be left in the vehicle. Also, the passenger may be unable to properly apply the passenger protection device. Using the passenger protection device (such as the seatbelt) for identifying if there is passenger still in the vehicle possibly causes a misidentification, failing to achieve a complete safety assuring objective.

Further referring to U.S. Pat. No. 6,937,143B2, a passenger detecting apparatus includes a weight sensor disposed on a seat of a vehicle, so as to detect the weight burden through the deformation of the seat when bearing a weight load, thereby identifying if the seat is occupied by a passenger. However, when applied for detecting a life form in the vehicle, the weight sensor is unable to identify whether the weight load comes from a life form or a non-life object, so that a misidentification is possibly caused.

Therefore, it is desirable to resolve the issue of misidentification in the in-vehicle life detection field.

SUMMARY OF THE INVENTION

For improving the issues above, an in-vehicle life-detection system and method thereof are disclosed. When the vehicle is in an engine off status with the driver not on the seat, a radar detection is carried out for detecting if there is a life form in the vehicle. If a life form is detected, the system sends out a warning signal for achieving the warning effect.

For achieving the aforementioned objectives, an in-vehicle life detection system is provided for detecting a life in a vehicle chamber, comprising a processor, an electromagnetic wave detection module electrically connected with the processor, and a warning module electrically connected with the processor. The processor receives an engine off signal and a driver absence signal and to save the engine off signal and the driver absence signal in a memory device connected to the processor, so as to generate a detection activation signal. The electromagnetic wave detection module receives the detection activation signal and is activated to emit an electromagnetic wave toward the vehicle chamber, and subsequently feeds an echo signal back to the processor, so as to carry out a life form detection and generate a reminder signal upon detecting the life form. The warning module receives the reminder signal and sends out a warning signal, so as to remind the driver that a life form is left in the vehicle when the vehicle is in the engine off status with the doors closed.

In accordance with an embodiment of the present invention, an in-vehicle life detection method is also provided, comprising a vehicle condition identifying step, a life form detecting step, and a warning step. In the vehicle condition identifying step, the condition of the vehicle is detected. When the vehicle is in the engine off status, an engine off signal is generated. When the driver is not on the seat with the doors closed, a driver absence signal is generated. In the life form detecting step, a detection activation signal drives the electromagnetic wave detection module to emit an electromagnetic wave toward the vehicle chamber, with an echo signal being subsequently fed back to the processor, so as to carry out the life form detection. When a life form is detected in the vehicle chamber, a reminder signal is generated by the processor. In the warning step, the warning module receives the reminder signal and sends out a warning signal, so as to remind the driver of a life form being left in the vehicle in the engine off status with the doors closed.

With such configuration, when the vehicle is in the engine off status with the driver being away from the seat, the electromagnetic wave detection module is driven to detect the life form in the vehicle chamber. When a life form is detected, a warning is sent out for achieving the warning effect. Due to the high accuracy and speed of the electromagnetic wave detection carried out by the electromagnetic wave detection module, the warning is immediately sent out when the driver leaves the seat, so that the driver or other people is allowed to immediately take the life form out of the vehicle, thereby preventing the life from being left in the vehicle without the capability of calling for help.

DETAILED DESCRIPTION OF THE INVENTION

Figure 1:
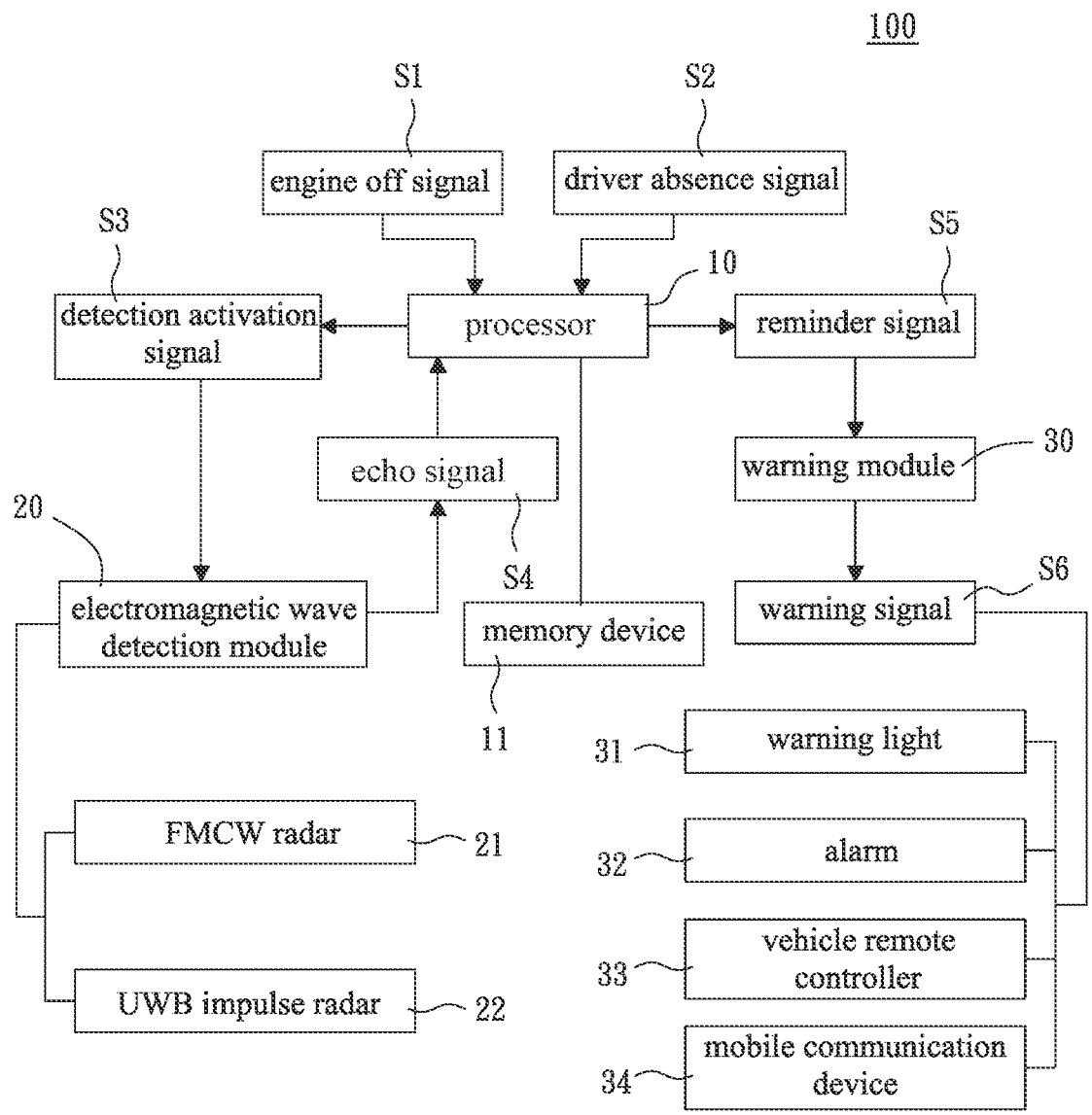
FIG. 1 is a block view of the detection system in accordance with an embodiment of the present invention.

The aforementioned and further advantages and features of the present invention will be understood by reference to the description of the preferred embodiment in conjunction with the accompanying drawings where the components are illustrated based on a proportion for explanation but not subject to the actual component proportion.

Referring to FIG. 1 to FIG. 7, an in-vehicle life detection system and method thereof are provided for detecting a life form in a vehicle chamber. The detection system 100 comprises a processor 10, an electromagnetic wave detection module 20, and a warning module 30 and is disposed in a vehicle 40.

The processor 10 is configured for receiving an engine off signal S1 and a driver absence signal S2 of the vehicle 40, and the processor 10 save the engine off signal S1 and the driver absence signal S2 in a memory device 11 connected to the processor 10, so as to generate a detection activation signal S3. In the embodiment, the processor 10 is allowed to be carried on the vehicle computer of the vehicle 40 or disposed on the control circuit of a single chip. The processor 10 is able to conduct a transmission through a signal connection in cooperation with a Controller Area Network (CAN) bus. The driver absence signal S2 is allowed to refer to a door closed signal or a door locked signal. The door closed signal is generated when the door at the driver seat is opened and then closed. The door locked signal is generated when the door is controlled to be locked by the control of a person.

The electromagnetic wave detection module 20 is electrically connected with the processor 10. The electromagnetic wave detection module 20 is configured to receive the detection activation signal S3 generated by the processor 10, accordingly emit an electromagnetic wave toward the vehicle chamber 41 of the vehicle 40, and feed an echo signal S4 back to the processor 10 for conducting the life form detection, with a reminder signal S5 being generated by the processor 10 when a life form is detected. Notably, the electromagnetic wave detection module 20 receives a reflection signal of the electromagnetic wave, and the identification of the existence of a life form is able to be carried out by the electromagnetic wave detection module 20, after which the echo signal S4 is fed back to the processor 10 upon identifying the existence of a life form. Alternatively, the identification of the existence of the life form is able to be carried out by the processor 10 after the processor 10 receives the echo signal S4.

The radar applied by the electromagnetic wave detection module 20 is allowed to be a frequency modulated continuous wave (FMCW) radar 21 or an ultra-wideband (UWB) impulse radar 22, or a combination of the two. In the embodiment, the radar applied by the electromagnetic wave detection module 22 is a combination thereof. Therein, the FMCW radar 21 is allowed to detect a movement of a life form in the vehicle chamber 41. The UWB impulse radar 22 is allowed to detect the regular breathe motions of a life form in the vehicle chamber by using different signals (such as frequency signal, amplitude signal, or orthogonal signal) that are sent out by the impulse wave toward an identical direction in a continuous time to determine the movement or delicate breathe motions of a life form at the identical position of the reflection signal. Further, the electromagnetic wave detection module 20 is integrated in a dome light 42 to be disposed on the roof of the vehicle 40. In the embodiment, the electromagnetic wave detection module 20 and the dome light 42 share the identical vehicle power source.

The warning module 30 is also electrically connected with the processor 10. The warning module 30 is configured for receiving the reminder signal S5 and sending a warning signal S6, so as to remind the driver of the existence of a life form in the vehicle 40 which is in the engine off status with the doors closed. In a preferred embodiment, the warning module 30 is electrically connected with a warning light 31 (head light and direction indicator) and an alarm 32 (vehicle horn or buzzer) of the vehicle 40. In different aspects, the warning module 30 is allowed to be electrically connected with a remote warning device through the wireless communication technique, so as to drive the remote warning device with the warning signal S6 to send out the warning. Said remote warning device refers to a vehicle remote controller 33 or a mobile communication device 34 which has a warning function.

Figure 2:
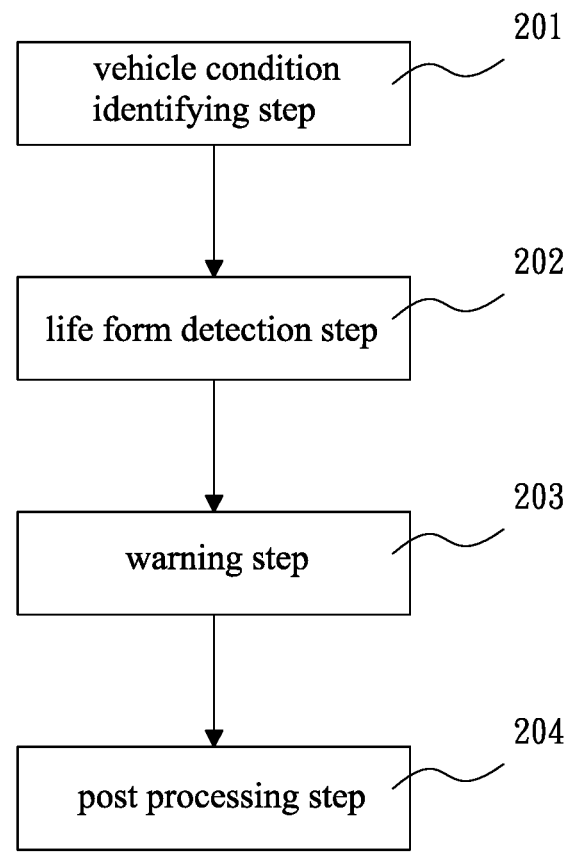
FIG. 2 is a flow chart of the detection method in accordance with an embodiment of the present invention.

With the foregoing configuration, a detection method 200 of the in-vehicle life detection system 100 will be illustrated below. Referring to FIG. 2, the detection method 200 comprises a vehicle condition identifying step 201, a life form detecting step 202 and a warning step 203. In the embodiment, a post processing step 204 is further included.

The vehicle condition identifying step 201 is applied for identifying the condition of the vehicle 40. When the vehicle 40 is in an engine off status, an engine off signal S1 is generated. When the driver leaves the seat with the doors closed, a driver absence signal S2 is generated. In the embodiment, the engine off status refers to that the electric switch (not shown) of the vehicle 40 is off, such that the engine off signal S1 is generated. Also, the door locked signal is a radio signal sent by the vehicle remote controller 33 for controlling the central locking system (not shown) of the vehicle 40 to lock the car door.

In the life form detecting step 202, the electromagnetic wave detection module 20 receives the detection activation signal S3, and is accordingly activated to emit the electromagnetic wave toward the vehicle chamber 41. After the electromagnetic wave is emitted, an echo signal S4 is generated and fed back to the processor 10. If a life form is detected, the electromagnetic wave detection module 20 receives an echo wave indicating an existence of a life form, such that the processor 10 generates the reminder signal S5.

Figure 3:
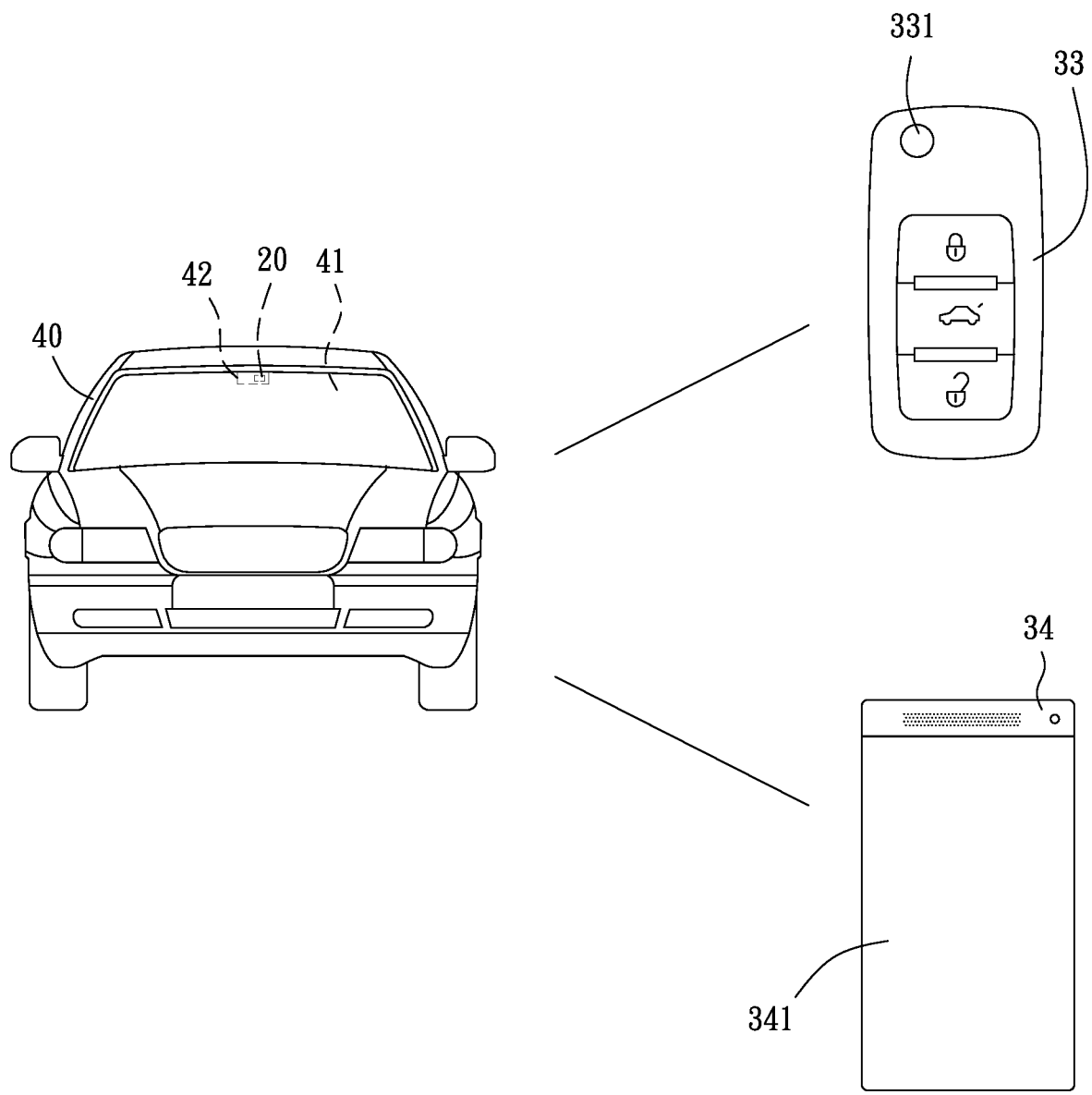
FIG. 3 is a schematic view illustrating the electrical connection between the vehicle, the vehicle remote controller, and the mobile communication device.

In the warning step 203, the warning module 30 receives the reminder signal S5 and sends out the warning signal S6, so as to warn the driver that there is still a life form left in the vehicle 40 when the vehicle 40 is in the engine off status with the doors closed. In the embodiment, when the warning signal S6 is sent, the warning light 31 flickers, and the alarm 32 sends out a warning sound. In addition, if a remote warning lights is used for warning, as shown by FIG. 3, the mobile communication device 34 (such as a smart phone or tablet computer) is installed with an application (APP) providing a warning function. By remotely activated by the warning signal S6, the speaker of the vehicle remote controller 33 or the mobile communication device 34 will send out the warning sound; also, an illumination device 331 of the vehicle remote controller 33 or a monitor 341 of the mobile communication device 34 sends out a light for achieving the warning effect. Furthermore, when the warning signal S6 is sent, the dome light 42 will also shine for warning.

In the post processing step 204, when the warning module 30 receives the reminder signal S5 and sends out the warning signal S6, if the vehicle 40 is in a locking status, the vehicle 40 will automatically unlock the doors (invalidating the locking status).

Figure 4:
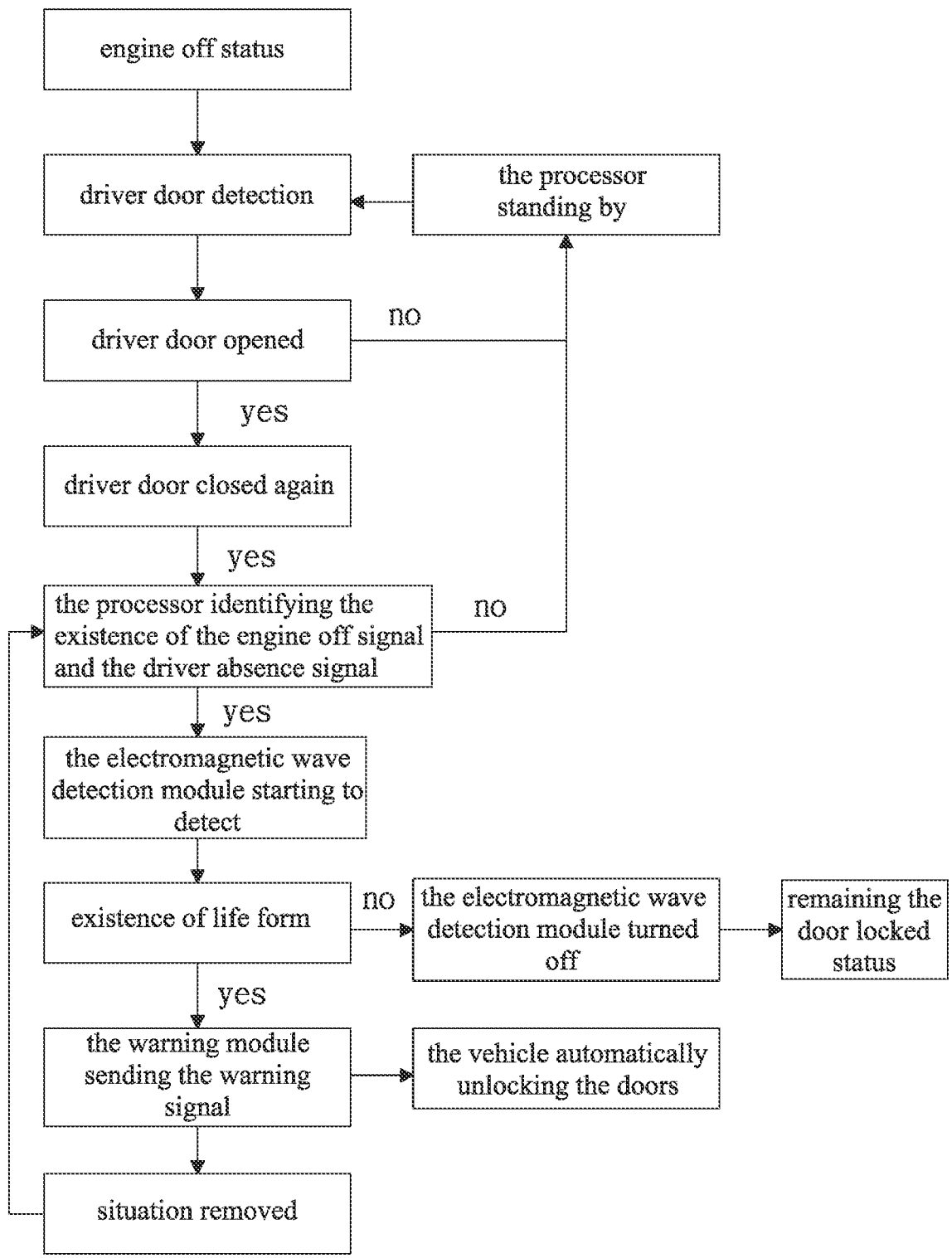
FIG. 4 is a flow chart illustrating the operation of the detection method in accordance with a first embodiment of the present invention.
Figure 5:
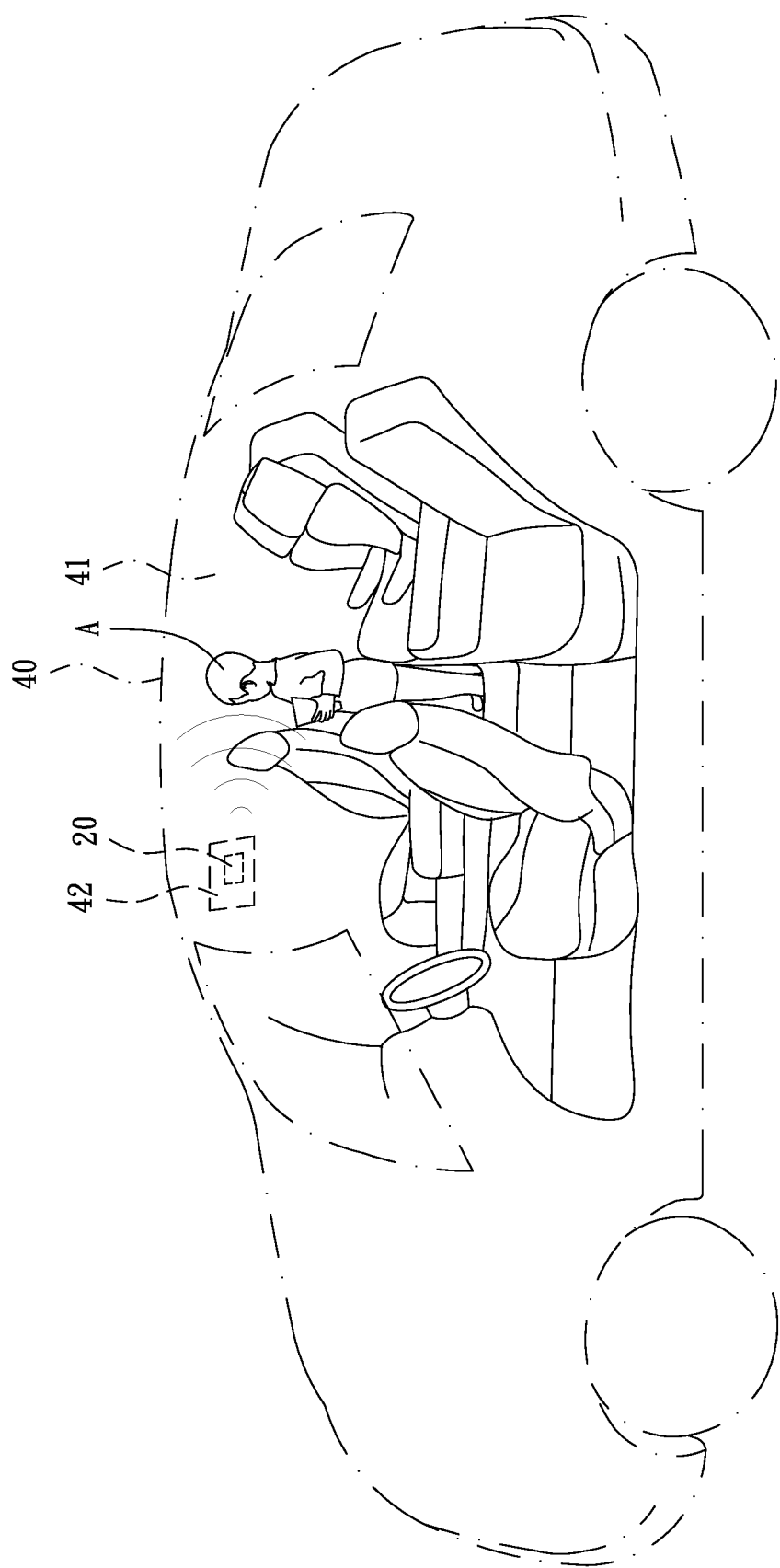
FIG. 5 is a schematic view illustrating the electromagnetic wave detection module emitting the electromagnetic wave with the frequency modulated continuous wave (FMCW) radar in the vehicle chamber for detection.
Figure 6:
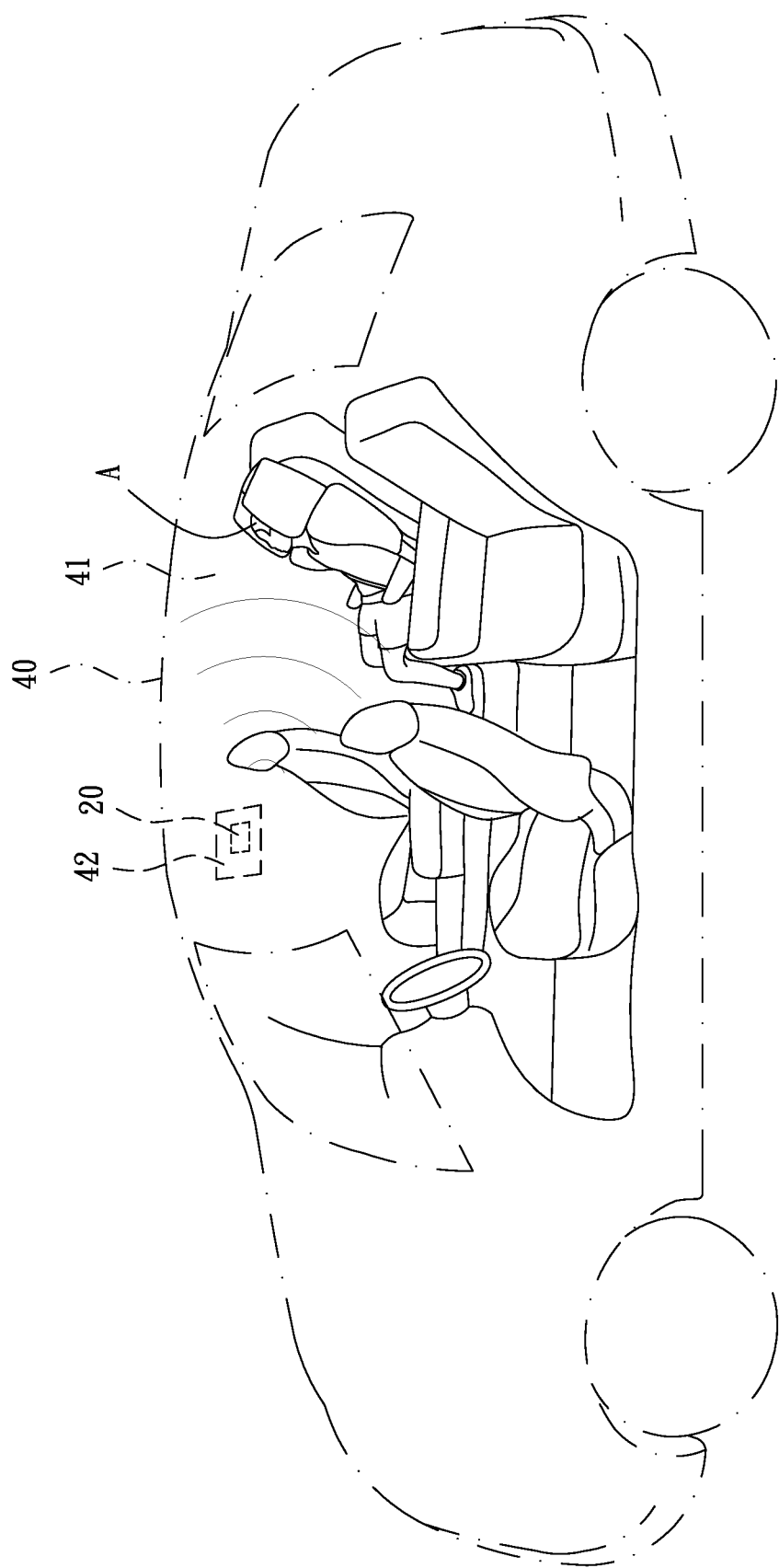
FIG. 6 is a schematic view illustrating the electromagnetic wave detection module emitting the electromagnetic wave with the ultra-wideband (UWB) impulse radar in the vehicle chamber for detection.

In the steps of the detection method 200, various aspects of embodiments may be included. Referring to FIG. 4, the detection flow of the first embodiment is shown. Therein, when the driver stops the vehicle 40 and switches the electric switch off, the vehicle condition identifying step 201 is carried out; at the meantime, the vehicle 40 is in the engine off status, so that the engine off signal S1 is generated and sent to the processor 10. The processor 10 detects if the motions of opening and closing the door at the driver seat occur. If the answer is negative, the processor 10 enters a stand-by status. If the answer is positive, it means that the driver firstly has opened the door to leave the vehicle 40 and subsequently closed the door; at this moment, the driver absence signal S2 is generated. After the processor 10 receives the engine off signal S1 and the driver absence signal S2, the processor 10 sends out the detection activation signal S3 which is received by the electromagnetic wave detection module 20.

Next, after receiving the detection activation signal S3, the electromagnetic wave detection module 20 begins the life form detecting step 202, so as to generate the electromagnetic wave for detecting the life form in the vehicle chamber 41. If a life form A (shown as the kid in FIG. 5) moves in the vehicle chamber 41, the FMCW radar 21 feeds the echo signal S4 which is generated corresponding to the movement of the life form A back to the processor 10. The processor 10 then generates the reminder signal S5 which is sent to the warning module 30. The warning module 30 beings the warning step 203, so as to send out the warning signal S6 for driving the warning light 31 to flicker and the alarm 32 to send out sound, or driving the remote warning device to send out the warning.

In the life form detecting step 202, in an alternative situation, when the life form A (shown as the kid in FIG. 6) is in the sleeping status, the UWB impulse radar 22 is applied for detecting the regular breathe motion of the life form A, such that the echo signal S4 is still generated and sent to the processor 10, and the processor 10 accordingly generates the reminder signal S5 which is then sent to the warning module 30. The warning module 30 beings the warning step 203, so as to send out the warning signal S6 for driving the warning light 31 to flicker and the alarm 32 to send out sound, or driving the remote warning device to send out the warning. Additionally, the vehicle 40 simultaneously unlock the doors, such that other person without the key is able to directly open the door. When the life form is removed from the vehicle 40, the process goes back to the vehicle condition identifying step 201 for repeating the detection of the driver absence signal S2.

In the life form detecting step 202, if the FMCW radar 21 and the UWB impulse radar 22 are unable to detect any signs of life form after a certain period of time, it is considered that there is no life form left in the vehicle 40. Therefore, the detections of the FMCW radar 21 and the UWB impulse radar 22 are turned off, and the doors of the vehicle 40 remain in the locking status.

Figure 7:
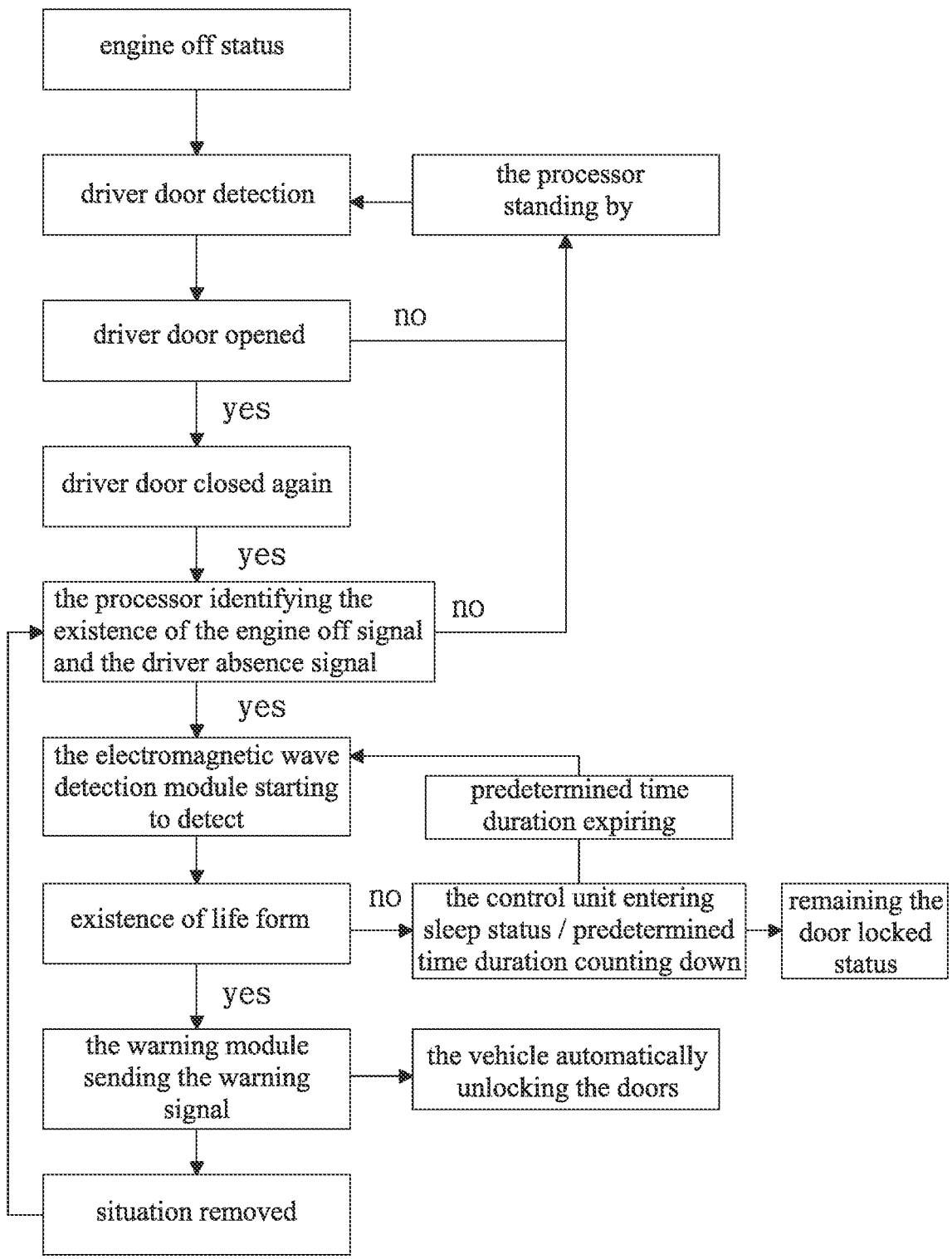
FIG. 7 is a flow chart illustrating the operation of the detection method in accordance with a second embodiment of the present invention.

Referring to FIG. 7, the detection flow in accordance with the second embodiment is illustrated. The difference between the first and second embodiments lies in that, when no life form is detected in the life form detecting step 202, the occasion may be that the life form is covered by objects, so that the echo signal S4 is temporarily unable to be received. For example, when a kitten or puppy hides under the seat to be undetectable, the detections of the FMCW radar 21 and the UWB impulse radar 22 will not be turned off; instead, the processor 10 temporarily enters a sleep status for a predetermined duration (such as 3 minutes) whose countdown simultaneously begins. When the predetermined duration is over, the life form detecting step 202 begins again, until the electromagnetic wave detection module 20 detects the life form. Therefore, the life form in the vehicle 40 will not be left because of being covered by objects.

To sum up, the present invention achieves following advantages.

When the vehicle 40 is in the engine off status, and the driver leaves the seat, the electromagnetic wave detection module 20 is activated for detecting if there is life form in the vehicle chamber 41. When a life form is detected, the warning signal S6 is sent for achieving the warning function. Also, the electromagnetic wave detection is carried out by the electromagnetic wave detection module 20 with a relatively high speed, so that the warning will be sent after the driver go away from the vehicle 40. Therefore, the driver is able to carry the life form out of the vehicle chamber 41 in time. If the driver has went away from the vehicle 40, other nearby person is also able to carry the life form out of the vehicle chamber 41. Also, the present invention does not apply an infrared sensor whose detection performance is easily affected by a high temperature. Also, the present invention prevents the misidentification of a non-life object which is placed on the seat. It is clear that the present invention is able to accurately detect the life form in the vehicle 40, thereby preventing the situation of a life form being left in the vehicle 40 and incapable of calling for help, so as to eliminate the possibility of coma or death situation of the life form which may accordingly happen. Also, compared with the conventional arts that use an image detection function, the electromagnetic wave detection does not generate the image of the detected person, assuring the privacy and preventing the leakage of personal information.

In the life form detecting step 202, if no life form is detected, in addition to deactivating the electromagnetic wave detection module 20 for assuring the safety, a repeating mechanism is further provided, whereby the processor 10 enters the sleep status and restarts the life form detecting step 202 after a predetermined time duration expires. Such operation repeats until the electromagnetic wave detection module 20 detects the life form in the vehicle 40, thereby preventing the life form from being undetectable while being covered by other objects.

The electromagnetic wave detection module 20, when being a UWB impulse radar 22, has a low power consumption property (generally lower than 200 mW). Therefore, the electromagnetic wave detection module 20 will not cause the exhaustion of the vehicle power source after running a longer detection operation. Also, the operation radius of the UWB impulse radar 22 reaches 10 meters. Thus, the UWB impulse radar 22 does not need to be disposed in a short distance with respect to the passenger. The space range in an ordinary sedan is covered by the detection range of the present invention.

Although particular embodiments of the invention have been described in detail for purposes of illustration, various modifications and enhancements may be made without departing from the spirit and scope of the invention. Accordingly, the invention is not to be limited except as by the appended claims.

What is claimed is:

1. An in-vehicle life detection system for detecting a life form in a vehicle chamber of a vehicle, the in-vehicle life detection system comprising:
   a processor configured to receive an engine off signal and a driver absence signal and to save the engine off signal and the driver absence signal in a memory device connected to the processor, so as to generate a detection activation signal; the driver absence signal referring to a door closed signal indicating the door being opened and then closed, or a door locked signal which controls the door to be locked after the door is opened and then closed;

an electromagnetic wave detection module electrically connected with the processor, the electromagnetic wave detection module being configured to receive the detection activation signal to be activated, so as to emit an electromagnetic wave and feed an echo signal back to the processor for detecting the life form; when the life form is detected, the processor generates a reminder signal; the processor having a sleep status which runs for a predetermined time duration; when the predetermined time duration expires, the sleep status is terminated, and the electromagnetic wave is emitted for detecting the life form again, until the electromagnetic wave detection module detects the life form in the vehicle; and a warning module electrically connected with the processor, the warning module being configured to receive the reminder signal and send out a warning signal, so as to indicate that the life form is left in the vehicle when the vehicle is in an engine off status with doors closed.

2. The in-vehicle life detection system of claim 1, wherein the electromagnetic wave detection module is selected from at least one of a frequency modulated continuous wave (FMCW) radar and an ultra-wideband (UWB) impulse radar; the frequency modulated continuous wave radar is configured to detect a movement of the life form in the vehicle chamber; the ultra-wideband impulse radar is configured to detect a regular breath of the life form in the vehicle chamber.

3. The in-vehicle life detection system of claim 1, wherein the warning module is electrically connected with a remote warning device through a wireless communication technique, so that the warning signal activates the remote warning device to warn.

4. The in-vehicle life detection system of claim 3, wherein the remote warning device is a vehicle remote controller or a mobile communication device which has a warning function.

5. The in-vehicle life detection system of claim 1, wherein the electromagnetic wave detection module is integrated in a dome light of the vehicle to be disposed on a roof of the vehicle; the electromagnetic wave detection module and the dome light share an identical vehicle power source; when the warning signal is sent, the dome light shines to warn.

6. A detection method of the in-vehicle life detection system of claim 1, comprising following steps:

a vehicle condition identifying step: identifying a condition of the vehicle; when the vehicle is in the engine off status, the engine off signal is generated; when a driver of the vehicle leaves a driver seat with the doors closed, the driver absence signal is generated;

a life form detecting step: activating the electromagnetic wave detection module with the detection activation signal, emitting the electromagnetic wave toward the vehicle chamber, and feeding the echo signal back to the processor for detecting the life form; when the life form is detected, the processor generates the reminder signal; if the electromagnetic wave detection module does not detect the life form, the processor enters a sleep status for a predetermined time duration; when the predetermined time duration expires, the life form detecting step is carried out again, until the electromagnetic wave detection module detects the life form in the vehicle; and a warning step: the warning module receiving the reminder signal and sending the warning signal, so as to warn that the life form is left in the vehicle when the vehicle is in the engine off status with the doors closed.

7. The detection method of claim 6, wherein in the vehicle condition identifying step, the door locked signal is a radio signal sent by a vehicle remote controller for controlling a central locking system of the vehicle to lock the doors of the vehicle.

8. The detection method of claim 6, wherein in the vehicle condition identifying step, when an ignition switch of the vehicle is off and the vehicle is in the engine off status, and the engine off signal is generated.

9. The detection method of claim 6, wherein the warning module is electrically connected with a remote warning device through a wireless communication technique; in the warning step, the warning signal actives the remote warning device to warn.

10. The detection method of claim 9, wherein the remote warning device is a vehicle remote controller or a mobile communication device which has a warning function.

11. The detection method of claim 6, further comprising a post processing step, wherein when the warning module receives the reminder signal and sends out the warning signal, the vehicle automatically unlocks the doors.

\* \* \* \* \*